US00PP12990P2

(12) United States Plant Patent
Glicenstein

(10) Patent No.: US PP12,990 P2
(45) Date of Patent: Sep. 17, 2002

(54) CHRYSANTHEMUM PLANT NAMED 'YONATALIE'

(75) Inventor: Leon Glicenstein, Lebanon, IN (US)

(73) Assignee: Yoder Brothers, Inc., Barberton, OH (US)

( * ) Notice: Subject to any disclaimer, the term of this patent is extended or adjusted under 35 U.S.C. 154(b) by 39 days.

(21) Appl. No.: 09/837,576

(22) Filed: Apr. 19, 2001

(51) Int. Cl.[7] ..... A01H 5/00
(52) U.S. Cl. ..... Plt./289
(58) Field of Search ..... Plt./289

*Primary Examiner*—Howard J. Locker
(74) *Attorney, Agent, or Firm*—C. A. Whealy

(57) ABSTRACT

A distinct cultivar of Chrysanthemum plant named 'Yonatalie', characterized by its upright plant habit; freely branching growth habit; uniform and freely flowering habit; decorative-type inflorescences; and bright yellow-colored ray florets.

1 Drawing Sheet

BACKGROUND OF THE INVENTION

The present invention relates to a new and distinct cultivar of Chrysanthemum plant, botanically known as *Chrysanthemum×morifolium* and hereinafter referred to by the name 'Yonatalie'.

The new cultivar is a product of a planned breeding program conducted by the Inventor in Salinas, Calif. and Fort Myers, Fla. The objective of the breeding program is to create new garden-type Chrysanthemum cultivars having inflorescences with desirable inflorescence forms, attractive floret colors and good garden performance.

The new Chrysanthemum originated from a cross made by the Inventor in June, 1995, in Salinas, Calif., of the Chrysanthemum cultivar Shelley, disclosed in U.S. Plant Pat. No. 7,993, as the female, or seed, parent with an unnamed Chrysanthemum proprietary seedling selection, as the male, or pollen, parent. The new Chrysanthemum was discovered and selected by the Inventor as a single flowering plant within the progeny of the stated cross grown in a controlled environment in Fort Myers, Fla. in November, 1996. The selection of this plant was based on its desirable inflorescence form, attractive ray floret color and good garden performance.

Asexual reproduction of the new cultivar by terminal cuttings taken in a controlled environment in Fort Myers, Fla. since January, 1997, has shown that the unique features of this new Chrysanthemum are stable and reproduced true to type in successive generations.

SUMMARY OF THE INVENTION

The cultivar Yonatalie has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Yonatalie'. These characteristics in combination distinguish 'Yonatalie' as a new and distinct cultivar:

1. Upright plant habit.
2. Freely branching, dense, full plants.
3. Uniform and freely flowering.

4. Decorative-type inflorescences.
5. Bright yellow-colored ray florets.

Plants of the new Chrysanthemum can be compared to plants of the female parent, the cultivar Shelley. In side-by-side comparisons conducted by the Inventor in Salinas, Calif., plants of the new Chrysanthemum differ from plants of the cultivar Shelley in the following characteristics:

1. Plants of the new Chrysanthemum are more mounded and uniform in growth habit than plants of the cultivar Shelley.
2. Plants of the new Chrysanthemum flower more uniformly than plants of the cultivar Shelley.
3. Plants of the new Chrysanthemum have larger inflorescences than plants of the cultivar Shelley.
4. Ray florets of plants of the new Chrysanthemum and the cultivar Shelley differ in color.

Compared to plants of the male parent, plants of the new Chrysanthemum differ in ray floret color.

Plants of the new Chrysanthemum can be compared to plants of the cultivar Holly, disclosed in U.S. Plant Pat. No. 7,992. In side-by-side comparisons conducted by the Inventor in Salinas, Calif., plants of the new Chrysanthemum differ from plants of the cultivar Holly in the following characteristics:

1. Plants of the new Chrysanthemum are more mounded and uniform in growth habit than plants of the cultivar Holly.
2. Plants of the new Chrysanthemum flower more uniformly than plants of the cultivar Holly.
3. Plants of the new Chrysanthemum flower about one week later than plants of the cultivar Holly.

BRIEF DESCRIPTION OF THE PHOTOGRAPHS

The accompanying photographs illustrate the overall appearance of the new Chrysanthemum. These photographs show the colors as true as it is reasonably possible to obtain in colored reproductions of this type. Colors in the photographs may differ slightly from the color values cited in the detailed botanical description which accurately describe the colors of the new Chrysanthemum.

The photograph at the top of the sheet comprises a side perspective view of a typical flowering plant of 'Yonatalie'.

The photograph at the bottom of the sheet comprises a close-up view of typical inflorescences of the cultivar 'Yonatalie'.

DETAILED BOTANICAL DESCRIPTION

In the following description, color references are made to The Royal Horticultural Society Colour Chart except where general terms of ordinary dictionary significance are used. The following observations and measurements describe plants grown in Salinas, Calif., under conditions which approximate those generally used in commercial garden Chrysanthemum production. One rooted cutting was planted in a 15-cm container in July, 2000 and plants were grown under natural season conditions. Plants were not pinched, that is, the terminal apex was not removed to enhance branching. Measurements and numerical values represent averages for typical flowering plants.

Botanical classification: *Chrysanthemum×morifolium* cultivar Yonatalie.

Commercial classification: Decorative-type garden Chrysanthemum.

Parentage:

*Female, or seed, parent.*—*Chrysanthemum× morifolium* cultivar Shelley, disclosed in U.S. Plant Pat. No. 7,993.

*Male, or pollen, parent.*—Unnamed *Chrysanthemum× morifolium* proprietary seedling selection, not patented.

Propagation:

*Type.*—Terminal tip cuttings.

*Time to initiate roots.*—About four days at 21° C.

*Time to produce a rooted cutting.*—About ten days at 21° C.

*Root description.*—White, fine and fibrous.

*Rooting habit.*—Freely branching.

Plant description:

*Appearance.*—Perennial herbaceous decorative-type garden Chrysanthemum. Inverted triangle; upright plant form. Stems initially upright, then somewhat outwardly spreading giving a uniformly mounded appearance to the plant. Freely branching with about 11 lateral branches per plant.

*Plant height.*—About 21 cm.

*Plant diameter.*—About 25 cm.

*Lateral branches.*—Length: About 16.5 cm. Diameter: About 5 mm. Internode length: About 1.25 cm. Aspect: Mostly upright. Texture: Pubescent. Color: 144A.

*Foliage description.*—Leaf arrangement: Alternate. Length: About 5.3 cm. Width: About 4.5 cm. Apex: Cuspidate to mucronate. Base: Mostly attenuate. Margin: Palmately lobed, sinuses mostly divergent. Texture: Both surfaces, pubescent; veins prominent on lower surface. Color: Young foliage upper surface: Darker than 147A. Young foliage lower surface: Darker than 147B. Mature foliage upper surface: 147A. Mature foliage lower surface: 147B. Venation, upper surface: 147B. Venation, lower surface: 146B. Petiole length: About 1.7 cm. Petiole diameter: About 2.5 mm. Petiole color, both surfaces: 146B to 147C.

Inflorescence description:

*Appearance.*—Decorative-type inflorescence form with quilled to spatulate-shaped ray florets. Inflorescences borne on terminals above foliage, arising from leaf axils. Disk and ray florets arranged acropetally on a capitulum. About 12 inflorescences per lateral; about 132 inflorescences per plant.

*Flowering response.*—Under natural season conditions, plants flower in late September in the Northern Hemisphere and continue to flower for at least three weeks depending on weather conditions.

*Inflorescence bud* (*before showing color*).—Height: About 6 mm. Diameter: About 8 mm. Phyllary color: 143A.

*Inflorescence size.*—Diameter: About 3.75 cm. Depth (height): About 1.4 cm. Disc diameter: About 2 mm or less, inconspicuous. Receptacle diameter: About 5 mm.

*Ray florets.*—Shape: Quilled to spatulate. Length: About 1.7 cm. Corolla tube length: About 1.2 cm. Width: About 3 mm. Apex: Acute, emarginate or dentate. Margin: Entire. Texture: Smooth, glabrous, satiny. Orientation: Initially upright and incurved, then perpendicular to the peduncle; quilled to concave. Number of ray florets per inflorescence: About 185. Color: When opening, upper and lower surfaces: 144A to 12A. Opened inflorescence, upper surface: 12A. Opened inflorescence, lower surface: 12A to 12B.

*Disc florets.*—Shape: Tubular, apex dentate. Length: About 6 mm. Width: Apex: About 1.5 mm. Base: About 1 mm. Number of disc florets per inflorescence: Less than 10. Color: Immature: 154A. Mature: Apex: 9A. Mid-section: 154D. Base: 155D.

*Peduncle.*—Aspect: Flexible, angled about 45 to 50° from the stem. Length: First peduncle: About 3.7 cm. Fourth peduncle: About 6.5 cm. Diameter: About 2.5 mm. Texture: Pubescent. Color: 144A.

*Reproductive organs.*—Androecium: Present on disc florets only. Anther color: 12A. Pollen: Scarce. Pollen color: 15A. Gynoecium: Present on both ray and disc florets.

*Seed.*—Seed production has not been observed.

Disease resistance: Plants of the new Chrysanthemum have not been shown to be resistant to pathogens common to Chrysanthemums.

Garden performance: Plants of the new Chrysanthemum have been observed to be tolerant to rain and wind.

It is claimed:

1. A new and distinct cultivar of Chrysanthemum plant named 'Yonatalie', as illustrated and described.

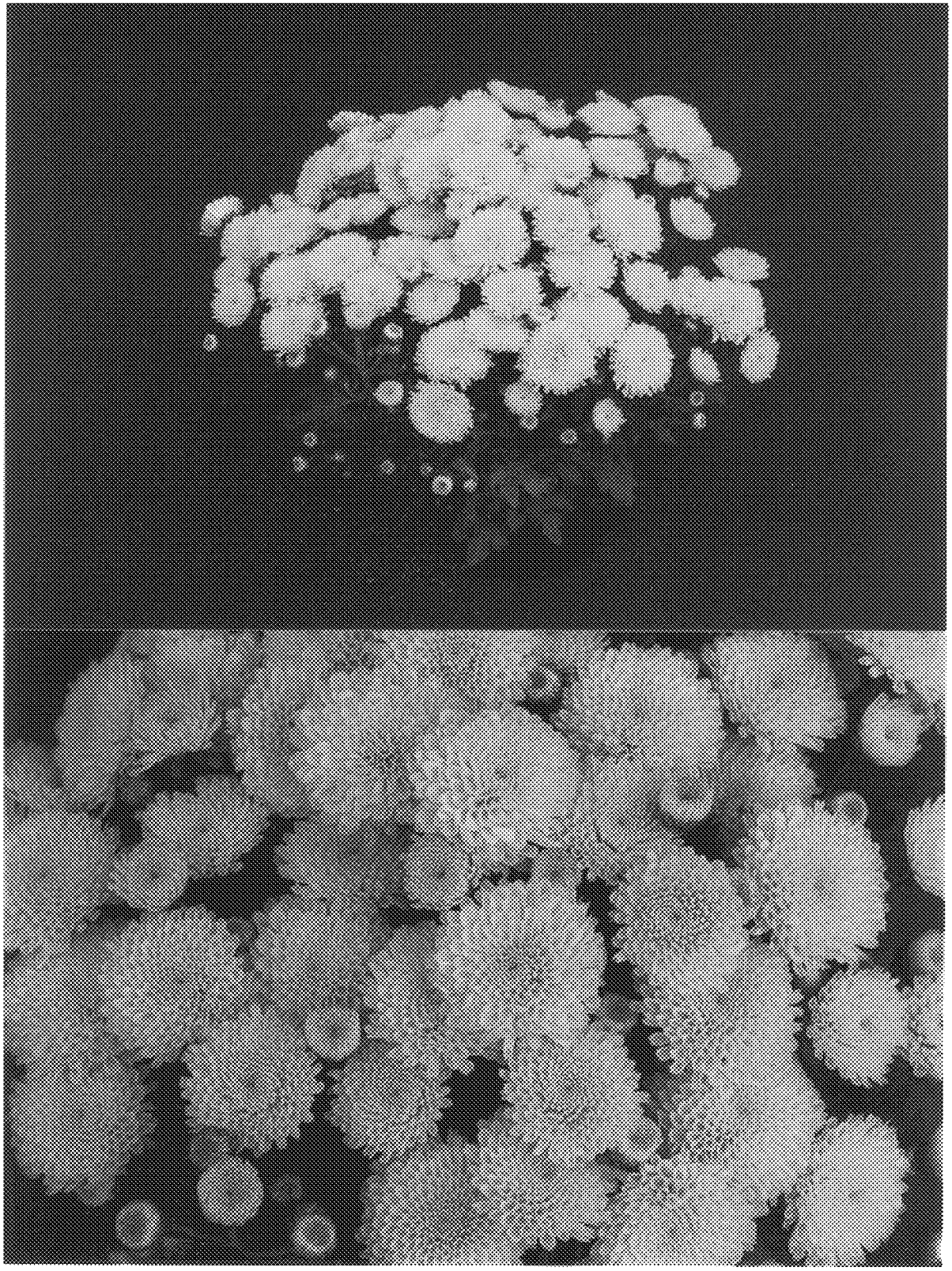

* * * * *